United States Patent [19]

Burian, deceased et al.

[11] Patent Number: 4,616,122
[45] Date of Patent: Oct. 7, 1986

[54] ELECTRICALLY HEATED FACIAL SAUNA VAPOR GENERATING APPARATUS

[75] Inventors: Paul D. Burian, deceased, late of Elmsford, N.Y., by Elissa Burian, administratrix; Raymond W. Kunz, Monroe, Conn.

[73] Assignee: Clairol Incorporated, New York, N.Y.

[21] Appl. No.: 496,875

[22] Filed: May 25, 1983

Related U.S. Application Data

[63] Continuation of Ser. No. 175,603, Aug. 6, 1980, abandoned.

[51] Int. Cl.⁴ .......................... H05B 1/00; F22B 1/28; F04B 43/04; A61H 33/12
[52] U.S. Cl. ...................................... 219/273; 4/537; 38/69; 38/77.8; 38/77.83; 68/222; 128/368; 219/275; 219/362; 239/136; 417/413
[58] Field of Search ............... 219/271–276, 219/362; 417/413; 68/222; 38/69, 75, 77.8–77.83; 239/135–138, 133; 43/128, 129; 261/141, 142; 4/535–537; 128/367, 368, 203.27

[56] References Cited

U.S. PATENT DOCUMENTS

| | | | |
|---|---|---|---|
| 2,146,431 | 2/1939 | Homoky | 219/275 |
| 2,194,535 | 3/1940 | Von Delden | 417/413 |
| 2,291,423 | 7/1942 | Tiscornia | 219/273 X |
| 2,402,575 | 6/1946 | Purpura | 38/75 |
| 2,429,441 | 10/1947 | Williams | 417/413 |
| 2,488,995 | 11/1949 | Thiberg | 417/413 |
| 2,576,976 | 12/1951 | Stagner | 219/273 |
| 2,606,272 | 8/1952 | Platt | 219/275 X |
| 2,809,589 | 10/1957 | Randolph | 417/413 |
| 3,069,092 | 12/1962 | Norvell | 239/133 |
| 3,119,004 | 1/1964 | Hoop | 219/271 X |
| 3,200,535 | 8/1965 | Hession | 239/133 X |
| 3,258,578 | 6/1966 | Ferris | 219/273 |
| 3,272,964 | 9/1966 | Carlos et al. | 219/271 |
| 3,371,852 | 3/1968 | Holt | 417/413 |
| 3,458,948 | 8/1969 | Curtis et al. | 219/275 X |
| 3,483,823 | 12/1969 | Palmer | 417/413 |
| 3,485,065 | 12/1969 | Frank | 68/222 |
| 3,546,428 | 12/1970 | Omohundro | 219/271 |
| 3,620,055 | 11/1971 | Blachly et al. | 68/222 |
| 3,675,449 | 7/1972 | Bluestein | 68/222 |
| 3,733,723 | 5/1973 | Takakuwa et al. | 38/69 |
| 3,781,519 | 12/1973 | Martin | 219/273 |
| 3,805,425 | 4/1974 | Spoida et al. | 68/222 X |
| 3,811,208 | 5/1974 | Vieceli et al. | 219/273 X |
| 3,825,374 | 7/1974 | Kondo | 417/413 |

FOREIGN PATENT DOCUMENTS 1958301 6/1971 Fed. Rep. of Germany ...... 219/275

Primary Examiner—A. Bartis
Attorney, Agent, or Firm—S. E. Krieger

[57] ABSTRACT

A portable apparatus for generating vapor for a facial sauna includes a housing enclosing a vented liquid storage tank having an inlet for receiving liquid to be vaporized and an outlet. An electrically heated vapor generator is located in the housing and receives liquid from the tank outlet through an electrically operated diaphragm pump for producing vapor which is discharged from an vapor outlet in the housing. The housing includes an elastic wall portion immediately adjacent and confronting the diaphragm operating armature of the pump. The elastic housing portion is manually displaceable inwardly of the housing for displacement of the pump diaphragm by the armature to prime the pump. An adjustable control is provided for regulating the pumping rate of the pump. The vapor generator is provided with anti-sputter baffles to prevent liquid droplets from being discharged with the vapor.

14 Claims, 22 Drawing Figures

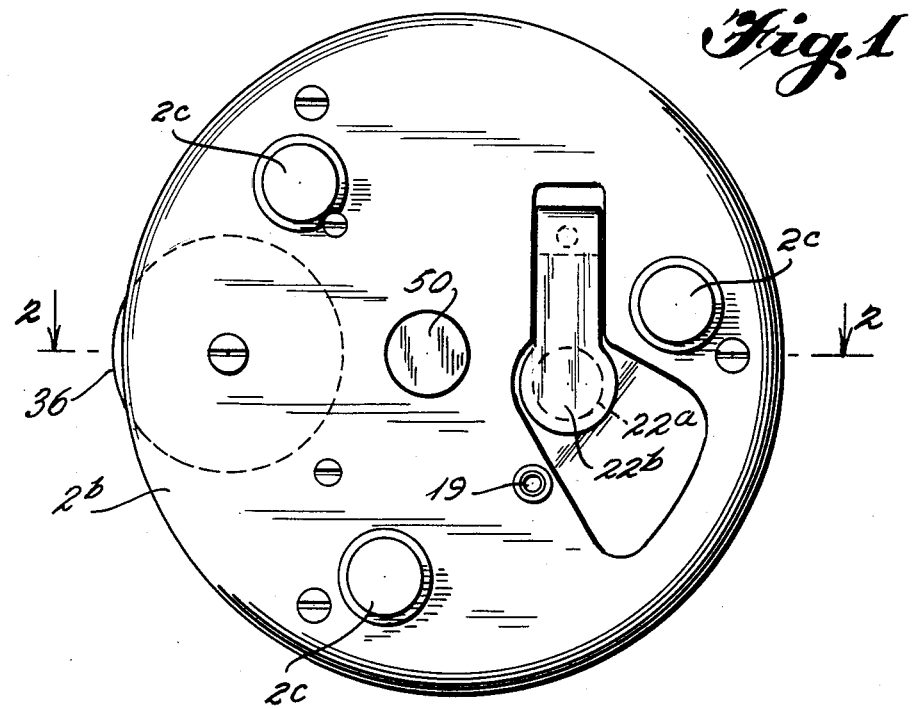
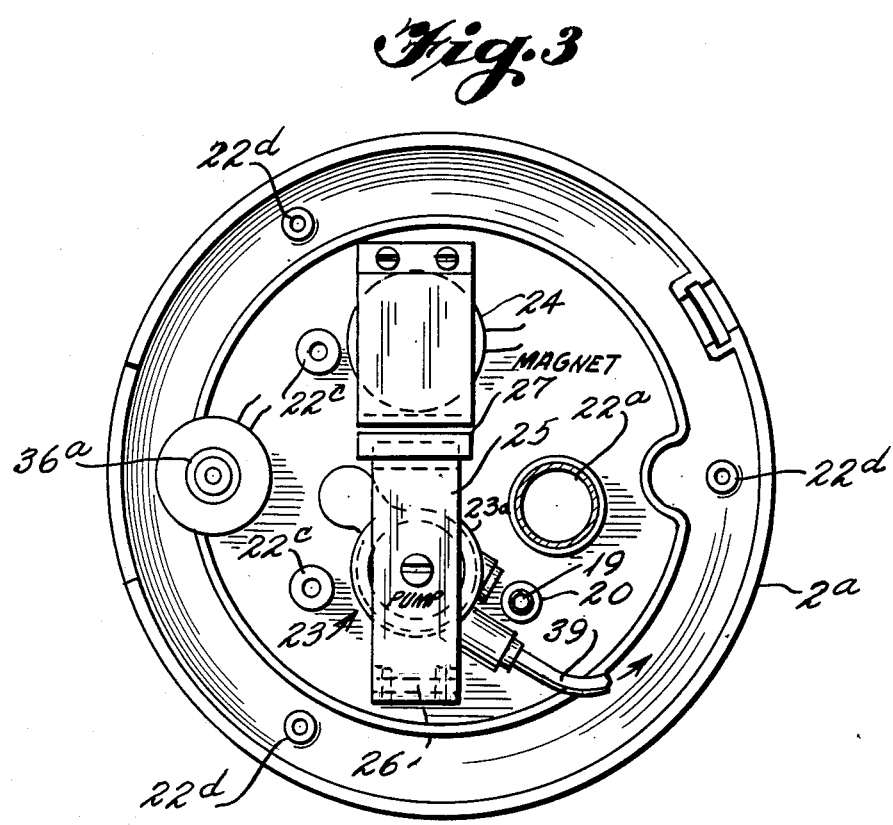

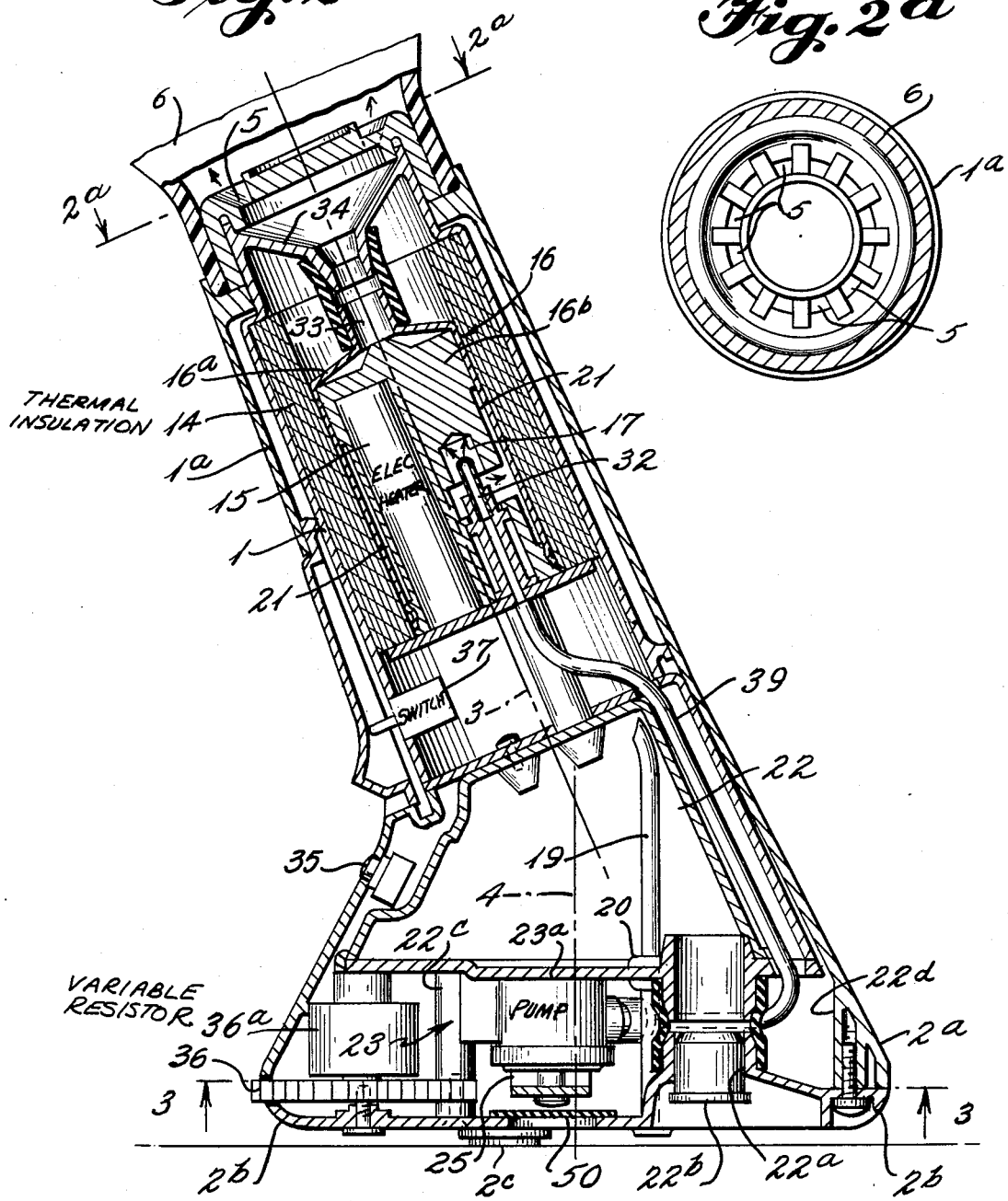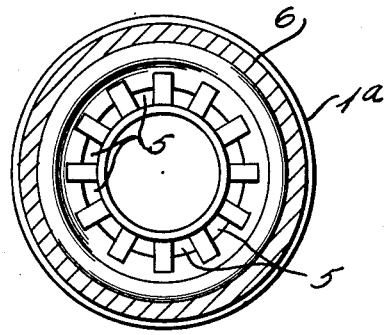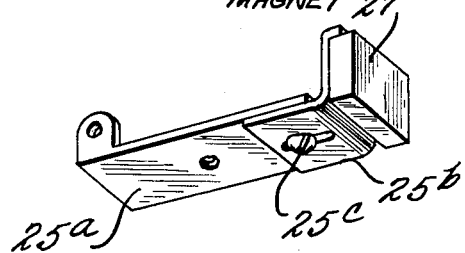

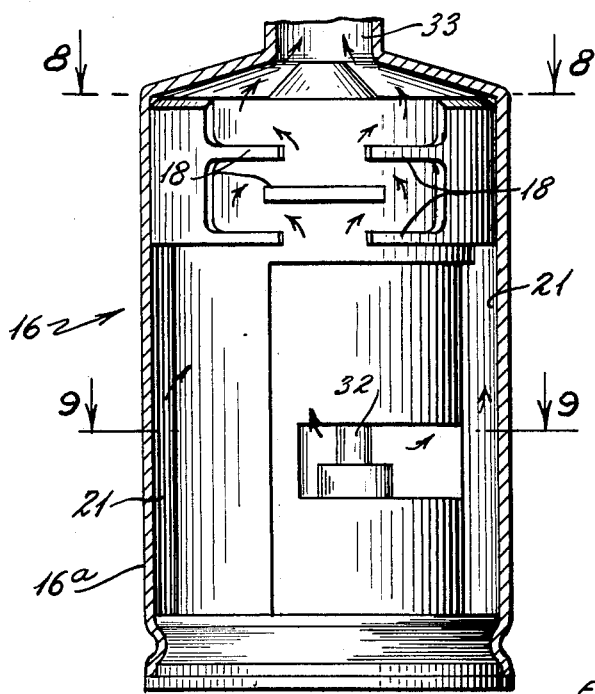
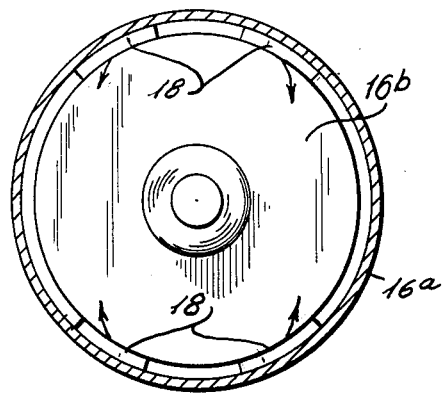
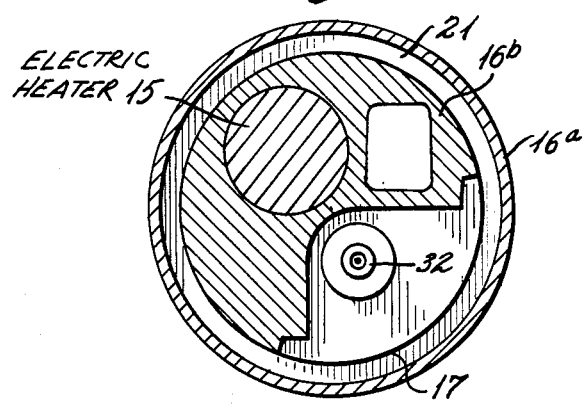
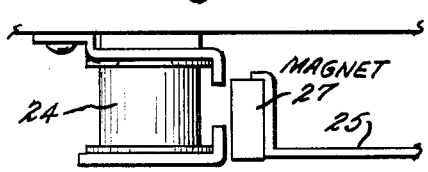
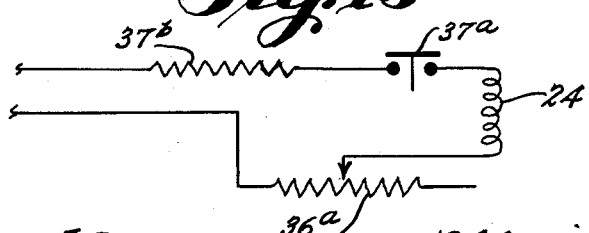
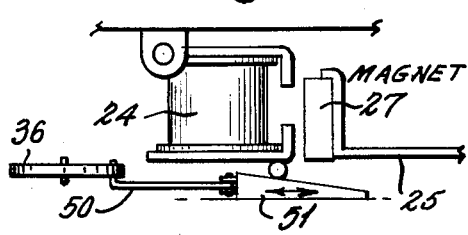
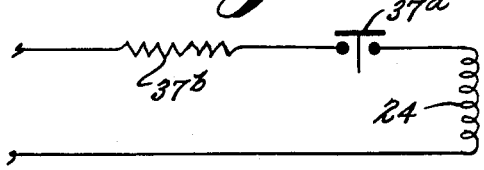

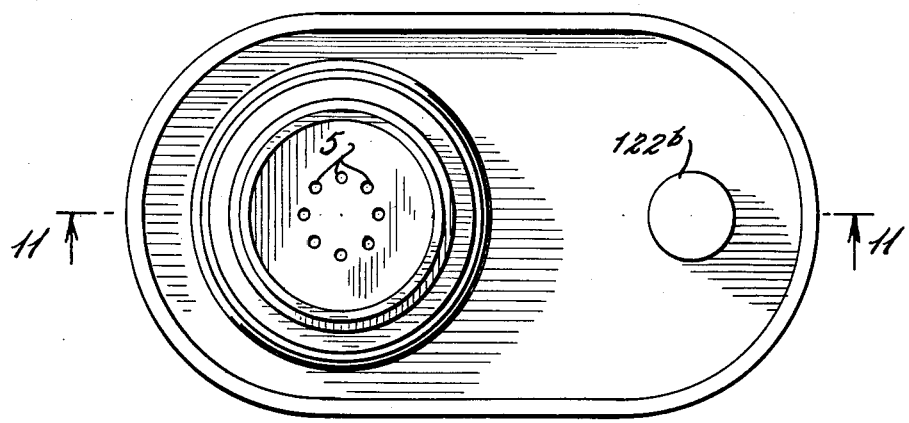
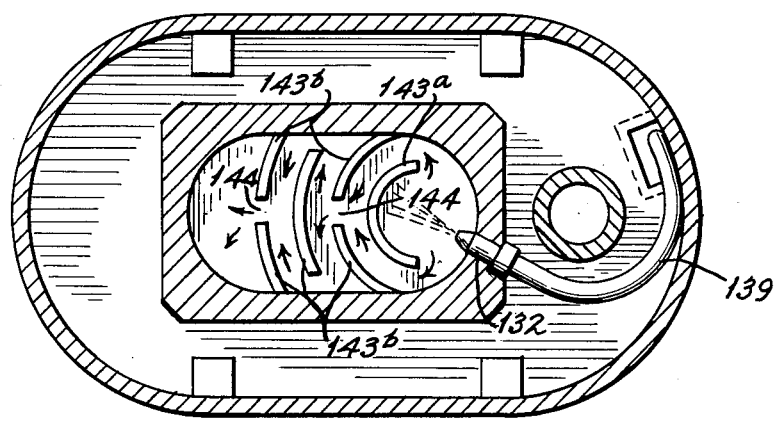
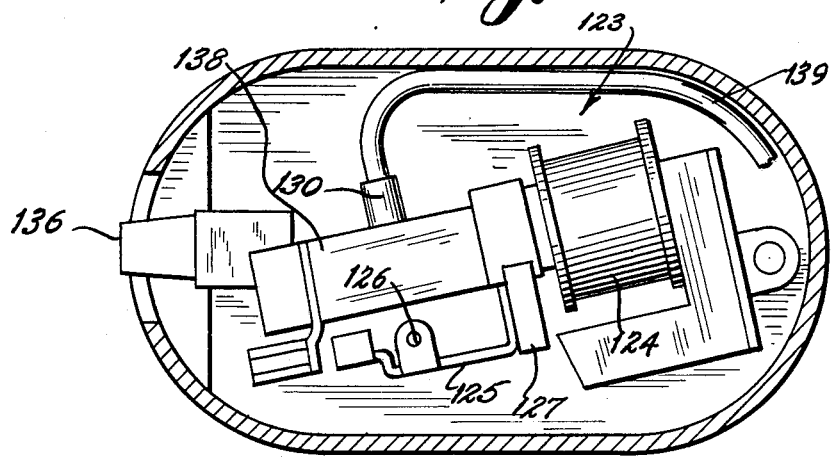

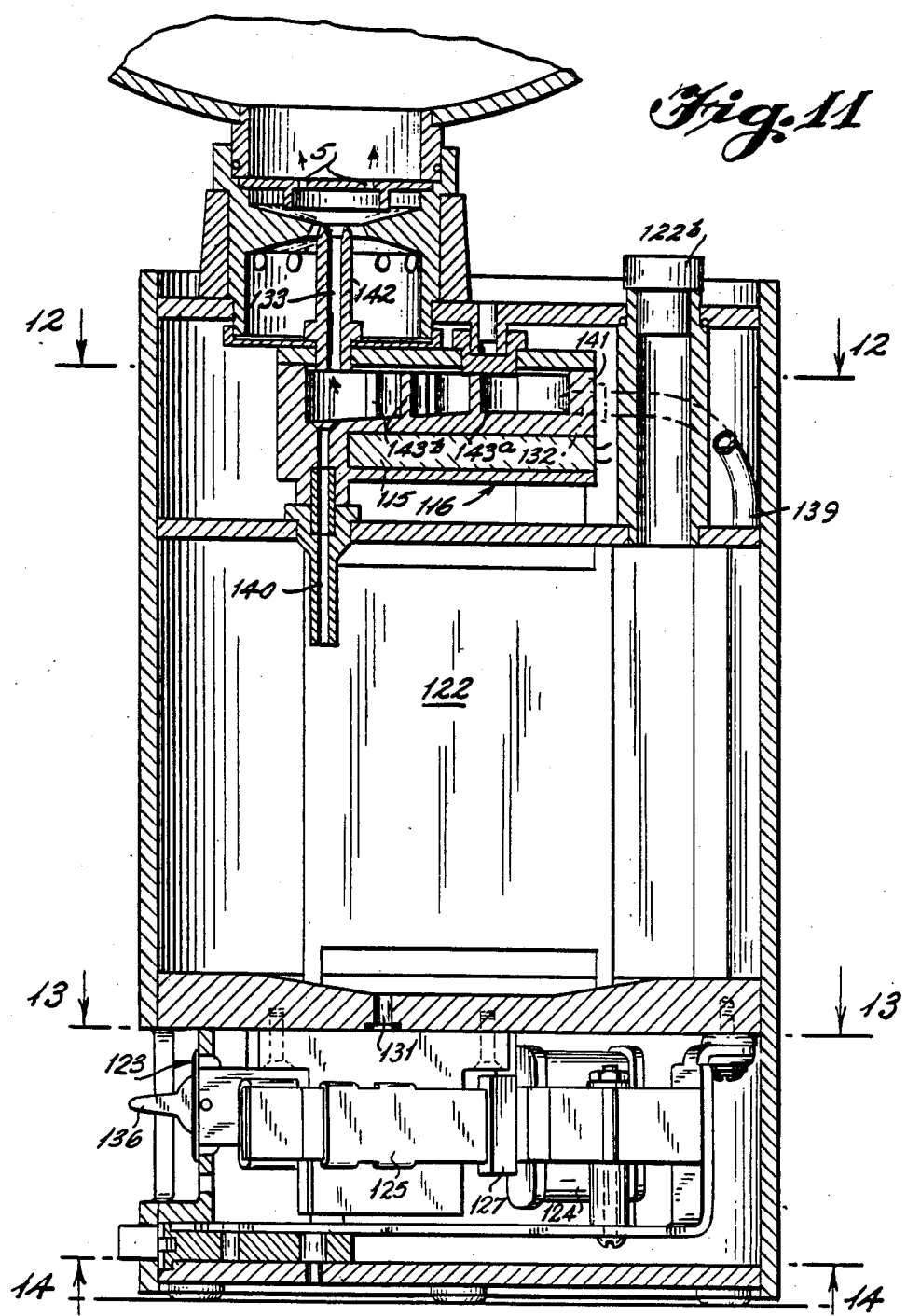

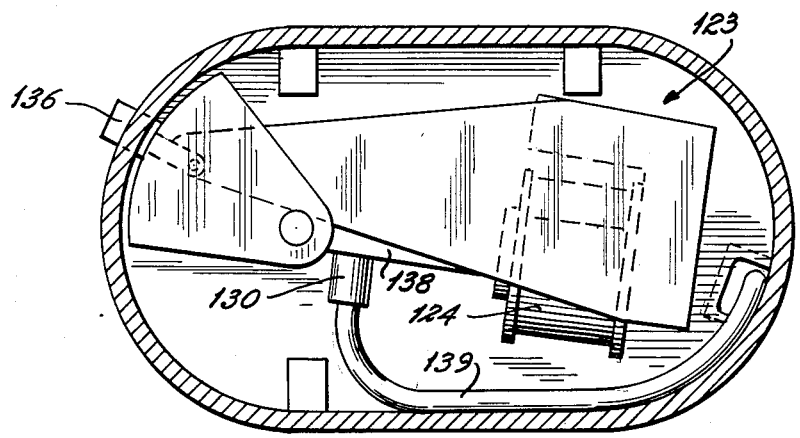
Fig.14
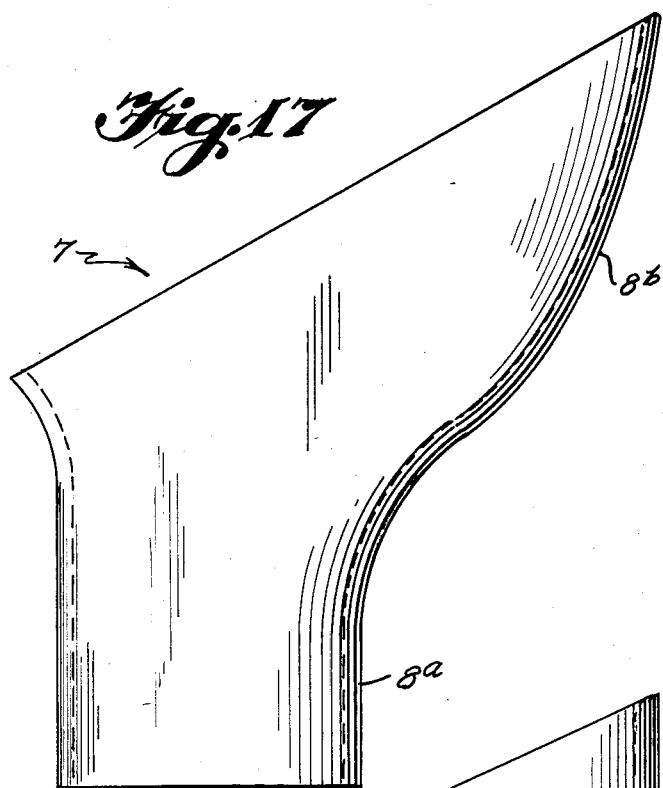
Fig.17
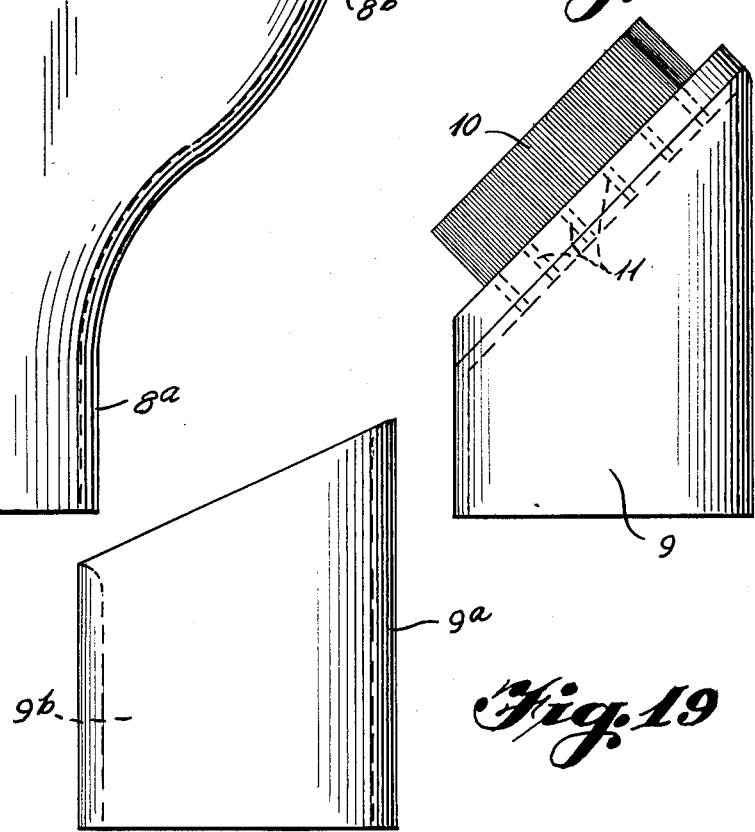
Fig.18
Fig.19

ELECTRICALLY HEATED FACIAL SAUNA VAPOR GENERATING APPARATUS

This is a continuation of application Ser. No. 175,603, filed Aug. 6, 1980, now abandoned.

DESCRIPTION

1. Field of the Invention

The invention generally relates to an apparatus for generating steam from water in a tank and particularly relates to a portable hand-held unit for generating steam for application to the face and body.

2. Description of the Prior Art

The prior art discloses various hand-held steam generating devices. U.S. Pat. No. 3,620,055 to Blachly, et al. describes a hand-held portable steamer for removing wrinkles from clothes. The steamer includes a reservoir connected to a finger-powered pump operated by a push-button which directs the pumped water through a tube to a steam generating means.

U.S. Pat. No. 3,733,723 to Takakuwa, et al. describes a hand-held portable steamer for finishing fabrics with steam. Water is pumped into the steam generator by a compressible water reservoir with spring-loaded action. The ejection of the steam which is created is controlled by a button-actuated valve.

Spoida, et al. in U.S. Pat. No. 3,805,425 describes a hand-held portable steamer having a brush attached circumferentially around the exit outlet for the steam discharge. Water is moved from the water tank by way of an intake through a finger operated pump device to a steam generator and through a plurality of outlets.

In U.S. Pat. No. 3,258,578, Ferris teaches a portable steaming device in which a fan is used to keep the casing cool, and the flow of water to the spray head is controlled by a plunger-type valve. Carlos, et al. in U.S. Pat. No. 3,272,964, describe a hand-held fabric steamer in which water enters the vaporized chamber due to gravity flow.

Frank in U.S. Pat. No. 3,485,065, discusses a portable clothes steamer with baffles interposed between the head and water chamber to prevent water from spilling and to prevent sputtering of the steam flow when the device is tilted.

The device of Omohundro, described in U.S. Pat. No. 3,546,428, includes a self-contained steam generator for treating hair with a spout which has a dual function of receiving water into the water reservoir and expelling water from the water tank.

U.S. Pat. No. 3,675,449 to Bluestein, discloses a steaming apparatus with removable brush in which the housing contains a two-section water storage tank and a steam head.

The above-cited references generally fail to provide sputter-free steam and fail to teach a structure which can be employed as a portable hand-held unit for applying steam to the face and body.

SUMMARY OF THE INVENTION

It is an object of this invention to describe a facial sauna employing a labyrinthine baffle including antisputter baffles to provide a sputter-free source of steam.

It is another object of this invention to describe a facial sauna having a condensate trap preventing condensed water from passing through the outlet.

It is another object of this invention to describe a facial sauna employing an electromagnetic pump.

It is another object of this invention to describe a facial sauna including a baffle structure for vaporizing water and a means for directing condensed water from the baffle structure back to the tank.

The facial sauna, according to the invention, is a portable device comprised of a housing containing a water reservoir tank; an electromagnetic coil driven pump; a control for the pumping rate of the pump; a water inlet nozzle receiving pressurized water from the pump; a series of baffles including anti-sputter baffles in a labyrinthine baffle disposed adjacent to a heating element for vaporizing the water exiting the nozzle; an exit path for the steam generated by the water contacting the heater cartridge surfaces; an outlet through which the steam exits; a trap for receiving steam which condenses back into water and for directing the condensed water back toward the baffles; a channel for returning the condensed water from the baffles back into the water reservoir tank; and a means for engaging attachments located over the outlet.

BRIEF DESCRIPTION OF THE DRAWINGS

These features and objects of the invention will become apparent to those skilled in the art by referring to the accompanying drawings in which:

FIG. 1 is a bottom plan view of the invention;

FIG. 2 is a longitudinal cross-sectional view taken on the line 2—2 of FIG. 1;

FIG. 2a is a view of the head of the invention taken on line 2a—2a of FIG. 2;

FIG. 3 is a bottom view along line 3—3 of FIG. 2;

FIG. 6 is a perspective view showing a modified form of an adjustable armature to activate the diaphragm according to the invention;

FIG. 7 is a side view of a heater cartridge according to the invention;

FIG. 8 is a cross-sectional view taken along line 8—8 of FIG. 7 showing the baffle arrangements;

FIG. 9 is a cross-sectional view taken along line 9—9 of FIG. 7;

FIG. 10 is a top plan view of another embodiment of the invention;

FIG. 11 is a cross-sectional view taken along line 11—11 of FIG. 10;

FIG. 12 is a cross-sectional view taken along line 12—12 of FIG. 11 showing the baffle structure according to the invention;

FIG. 13 is a cross-sectional view taken along line 13—13 of FIG. 11 showing the pumping means according to the invention;

FIG. 14 is a cross-sectional view taken along line 14—14 of FIG. 11;

FIGS. 15 and 15a show a fixed embodiment of a control means for the coil moving the diaphragm according to the invention;

FIGS. 16 and 16a show a movable embodiment of a control means for the coil for moving the diaphragm according to the invention;

FIG. 17 is a view of a mask attachment for the inventive device;

FIG. 18 is a view of a brush attachment for the inventive device; and

FIG. 19 is a view of a concentrator or spot treatment attachment for the inventive device.

As shown in FIGS. 1, 2 and 3, the facial sauna, according to the invention, is enclosed in a housing having an upper tubular portion 1, enclosed within an outer shell 1a, and a lower conical portion formed by parts 2a and 2b. The base 2b rests on three feet 2c when in an upright position. The axis 3 of the tubular portion 1 forms an acute angle with the axis 4 of the lower conical portion. The acute angle facilitates the placement of the facial sauna on a table so that steam is directed toward the face or other part of the body.

Figure 4:
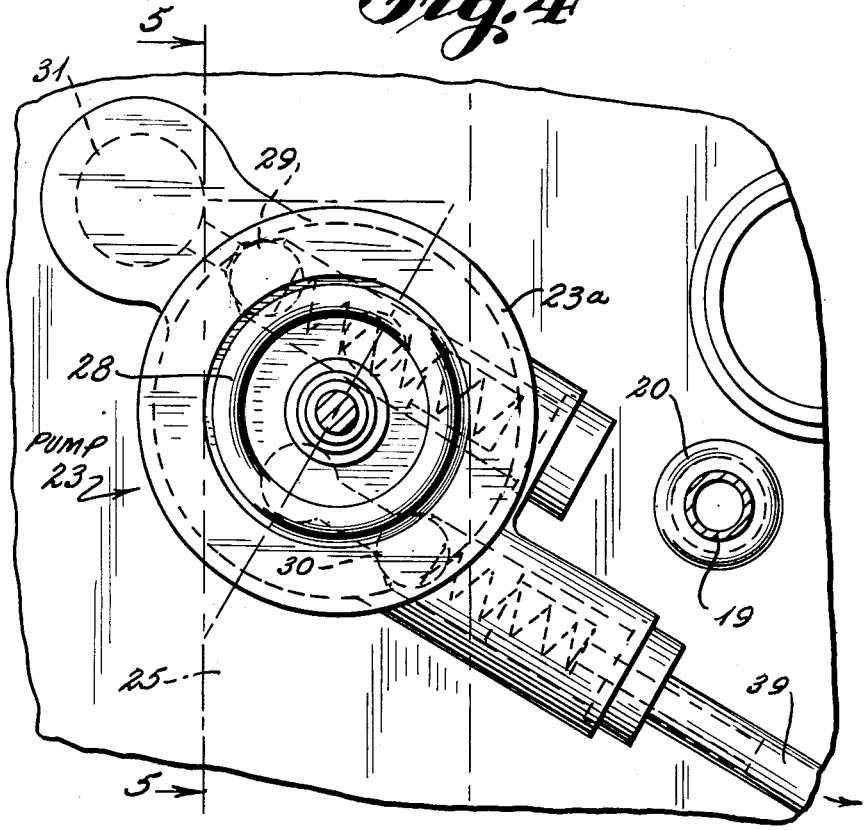
FIG. 4 is an enlargement view of the pump shown in FIG. 3.

The upper part of the tubular portion 1 includes outlets 5 and is engageably coupled to an attachment 6, of which only a connecting part is shown. The attachment may be a face mask 7 having a substantially cylindrical lower portion 8a for mounting on the tubular portion 1 of the facial sauna, as shown in FIG. 17. The mask includes an upper portion 8b having an expanded opening at its top for directing steam to a wider area than provided by outlet 5, and particularly to an area in which a user's face is located. In addition, a facial brush attachment, shown in FIG. 18, may be attached at its lower portion 9 to the tubular portion 1. The brush includes bristles 10 at its steam outlet side, and connecting channels 11, shown symbolically in the Figure, for passing steam from lower portion 9 through the bristled portion and to the user's face. Also, a concentrator or spot treatment attachment, shown in FIG. 19, having a diagonally truncated cylindrical shape may be attached at its lower portion 9a. The attachment confines the exiting steam to the diameter of the attachment for local topical use. The diameter of the steam exit 9b does not exceed the diameter of the bottom attaching portion.

A heater 15 is employed within the facial sauna and is generally a cylindrical resistance-type heater axially arranged within the housing. The heater is located within a heater cartridge, or boiler, generally referred to by reference character 16 and illustrated in FIGS. 7–9. The heated cartridge includes a metallic body 16b within which the electric heater 15 is embodied.

As further seen in FIGS. 2 and 7–9, heater cartridge 16 is provided with a cover 16a. The space between cartridge cover 16a and outer shell 1a, or upper housing 1, may be filled with thermal insulation 14, which may be made of bonded thin aluminum foil and insulation. The foil may be interrupted to avoid heat loss through a continual spiral surface of aluminum.

Cartridge 16 is a cylindrical member having a boiler cavity 17 and a plurality of anti-sputter baffles 18. The boiler cavity 17 is located within the heater cartridge 16. The walls of the cavity 17 are the first hot surface with which the water comes in contact in the boiler. Accordingly, the cavity is formed in a metallic casting, preferrably having a large surrounding mass to enable enhanced heat storage ability. The anti-sputter baffles 18 which are a pair of non-contacting two-stage labyrinths, are located on opposite sides of the cartridge, as shown in FIG. 8. The baffles 18 permit steam, but not non-vaporized fluid, to exit the device. Such selectivity is achieved by causing the fluid passing along the outer part of the cartridge 16 to travel in a more or less zig-zag pattern.

An air vent tube 19 extends through bottom portion 2b of the device, and into a water tank 22 acting as a fluid reservoir. A rubber grommet 20 provides a watertight seal between the air vent tube 19 and the bottom wall of tank 22. This air vent tube 19 allows atmospheric air to replace water withdrawn from the water tank 22.

The heater cartridge 16 is located within and is concentric with the tubular portion 1. Water tank 22 is located below the cartridge 16 for holding the water which is to be vaporized into steam. The tank 22 has a convenient fill opening 22a, sealed by a plastic plug 22b, so that is may be filled by the user when the unit is inverted. The heater cartridge 16 provides sufficient heat to evaporate water pumped at the rate of about 2 to 5.5 cc/min into it. This eliminates the need for a water return line as described in the alternate embodiment shown in FIG. 11.

The base of the tank 22 and bottom cover 2b are rigidly attached by means of post spacers 22c which are conveniently attached with screws. The number, location and configuration of the spacers 22c can be of any convenient design. A preferred arrangement would be spacing at 120° intervals near the outside edge of the base of tank 22. The spacers may be cylindrical or any other convenient outside shape. The height of the spacers depends on the size of the unit. A preferred embodiment has spacers of approximately ¼ to one inch long. The spacers may be separate units, but it is preferred that they be molded as integral parts of the base of the tank 22, which avoids leakage problems caused by screws. Also bosses 22d, at least three, molded as a part of lower housing 2a, are provided for attaching bottom cover 2b to lower housing 2a.

Figure 5:
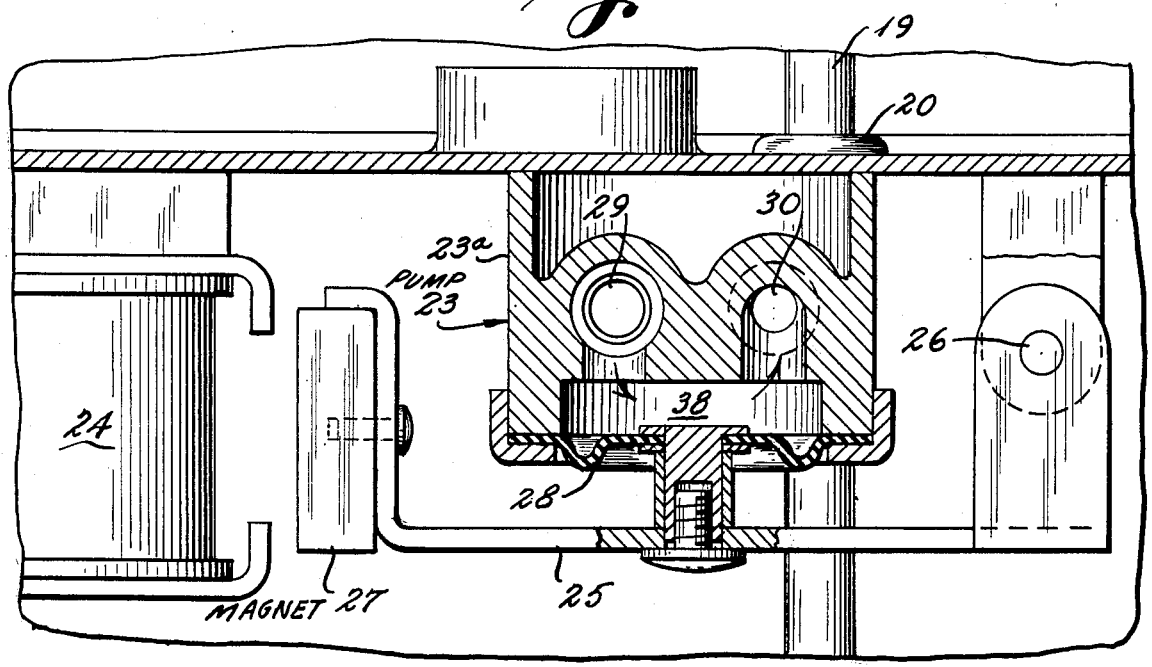
FIG. 5 is a cross-sectional view taken along line 5—5 of FIG. 4.

As shown in FIGS. 1, 2, 3, 4 and 5, a pump means 23 is located immediately below the tank 22. Pump 23 includes a pump housing 23a an electromagnetic coil 24, an armature 25 with one end connected to an armature pivot 26 and the other end supporting a magnet 27. The armature 25 may comprise a single piece extending from pivot 26 to the end supporting magnet 27. Alternatively, the armature may be comprised of two overlapping pieces 25a and 25b which are in sliding relationship as shown in FIG. 6. A clamping screw 25c holds the pieces together through an elongated hole in one of the pieces, enabling adjustments at assembly to maintain a prescribed gap between magnet 27 and coil 24. A diaphragm 28 is connected to the armature 25, and an intake valve 29 and an output valve 30 are in communication with the diaphragm 28. When an alternating current is applied to the electromagnet coil 24, the magnet 27 is caused to vibrate about the armature pivot 26 thereby moving the diaphragm 28 toward and away from the intake valve 29 and output valve 30. A tank outlet 31 is connected to the intake valve 29 and the outlet valve 30 is connected to the water inlet nozzle 32 by a tube 39.

The pump 23 is advantageously disposed in an orientation wherein the diaphragm 28 vibrates vertically. It is appreciated, however, that the pump may be differently oriented. For example, a horizontally vibrating magnet is possible, but the vertical orientation is preferred.

Immediately above the heater cartridge 16 located within bore 21, the bore tapers into a throughneck portion 33 for directing the vaporized steam from the heater cartridge 16 therethrough, to and through outlets 5 as shown in FIG. 2. The neck 33 is connected to an outlet funnel 34 disposed below outlets 5.

It is contemplated that the pump means 23 may be provided with a steam rate control knob 36 shown in FIG. 1, which can selectively limit the movement of the armature 25 by pivoting the coil 24 so as to cause the coil's electromagnetic field to rotate out of alignment with the plane of the magnet 27, thus restricting vibratory travel of the armature and thereby controlling the amount of water which is pumped by the diaphragm 28 in combination with the intake valve 29 and output valve 30. As shown in FIG. 16, a linkage arm 55 is pivoted by the control knob 36 to limit the action of armature 25 with wedge 51. As shown in FIG. 16a, the electrical circuitry of the control shown in FIG. 16 includes a switch 37a, a dropping resistor 37b, and coil 24, in a series connection, receiving current from the power supply such as 120 V, 60 Hz a-c current. Alternatively, an electrical control means may be used. Referring to FIGS. 3, 15 and 15a, control knob 36 is attached to a variable resistor 36a to regulate the current through coil 24 which, in this embodiment, does not pivot, unlike the arrangement shown in FIG. 16. To change from one setting to another, a user turns knob 36, thus varying the resistance of resistor 36a, changing the current in coil 24, thus causing the vibratory travel of the magnet 27 to vary, and thereby changing the amount of water pumped by the diaphragm 28. Each setting of resistor 36a provides a particular current setting, and thus, a particular travel limit of magnet 27 and a corresponding water pumping rate. In a preferred embodiment, approximately 2 to 5.5 cc/min. of water is pumped. In order to accomplish this, the fixed and variable resistor in the circuit, 37b and 36a, respectively, should be selected so that a usable range of the variable resistor is available between about 2500 and 7500 ohms. The variable resistor 36a may thus be a 10,000 ohm potentiometer, so that adjustments can be made to offset manufacturing variations and the control knob 36 is marked and attached accordingly. It is appreciated that the value of the potentiometer resistance would vary as the fixed resistance changes.

Variations in the above ranges can be made depending on the strength of the magnet, the gap between the magnet and the coil, and other structural variations. A simple on-line measurement of the water pump rate can be made to determined the final adjustments.

Furthermore, the facial sauna, according to the invention, is conveniently provided with an ON/OFF switch 37a which can be used as a momentary switch or locked in either position at the user's discretion. A pilot light 35 may be provided to indicate to the user whether the switch 37a is in its ON or OFF position.

In order to prime pump 23 while the appliance is in the upright position after filling, elastomatic diaphragm 50 is displaced upward, with a finger, for example, causing the armature 25 and the pump diaphragm 28 to move more than when the armature 25 is magnetically driven, thus increasing the effective displacement of the pump 23 cleaning it of air bubbles. The facial sauna operates as follows: Alternating current applied to the electromagnetic coil 24 forces the magnet 27 to oscillate vertically. As the armature 25 and diaphragm 28 are moved away from the intake valve 29, water is drawn from the tank 22 into a pumping chamber 38. As the armature 25 and diaphragm 28 pivot toward the output valve 30, the intake valve 29 seals and the water is forced through the output valve 30 via a tube 39 to the water inlet nozzle 32. Water then impinges upon boiler cavity 17 and is immediately vaporized, passing out cavity 17 and rising through bore 21 in zig-zag passes through anti-sputter baffles 18, through the neck 33, and finally through outlets 5 to the engaged attachment 6.

The continuous water supply from the pumping means further enhances the movement of the vaporized water through the heater cartridge 16.

Vapor, which condenses into water, is directed back through neck 33 along the surface of funnel 34, and drips back into contact with the heater cartridge 16 for vaporization. Water cannot condense within the heater cartridge 16 because all surfaces thereof are too hot, having temperatures exceeding 220° F., for example.

It is appreciated, however, that less powerful heaters may be used, necessitating the use of a drain and drain valve in a condensate line to the water tank.

FIGS. 10-14 illustrate an alternative embodiment of the invention wherein similar structures having an identical function to those of FIGS. 1-9 have the same reference characters with a prefix of 1 added thereon. As illustrated in FIG. 11, the heater cartridge 116, enclosing heater 115, is horizontally mounted within the housing of the alternative embodiment. Therefore, the water inlet nozzle 132 is mounted at an end 141 of the cartridge 116.

As particularly illustrated in FIG. 12, it is contemplated that a flash-off baffle 143a, which is the first baffle with which the water comes in contact, and the anti-sputter baffles 143b have an arcuate shape with alternating apertures 144 for guiding the vaporized water in a zig-zag pattern through the cartridge 116. Because a flash-off baffle is used in heating the water, the mass surrounding the cavity, and hence, the heat storing ability thereof, is reduced. A drain 140, having a one-way drain valve therein (not shown) is accordingly provided to facilitate the return of water to the tank. The drain 140 is also vertically mounted below cartridge 116. The drain 140 and the inlet nozzle 132 are mounted at opposing ends of the cartridge, as seen in FIG. 12.

As shown in FIGS. 11, 13 and 14, a pump means 123 is located immediately below a water tank 122. Pump 123 includes an electromagnetic coil 124, an armature 125 with one end connected to an armature pivot 126 and the other end supporting a magnet 127, a pumping chamber 138 and an output valve 130. As in the previous embodiment of the invention, this embodiment may also be provided with a steam rate control knob 136.

In operation, water in tank 122 flows through the tank outlet 131 into a pumping chamber 138. It is then forced through the output valve 130 into the water inlet nozzle 132 via a tube 139. The water then travels in a similar manner past the baffles and out the neck portion 133. A condensate trap 142, shown in the embodiment illustrated in FIG. 11, is comprised of a cylindrical chamber. One critical feature of the illustrated embodiment of FIG. 11 is the axial alignment between the neck 133 and the drain 140. In this embodiment, water condensing within the condensate trap 142, or within the baffle cartridge 116, immediately passes back through the drain 140 and is returned to the tank for pumping once again by the pump means 123.

As shown in FIG. 11, the illustrated embodiment allows a location of a filler neck plug 122b at the top of the facial sauna apparatus for convenient filling of the tank 122.

While the foregoing description is in terms of water and steam, it is understood that other liquids may be used, and that the resulting vapor may include components other than steam.

Various changes can be made in the details of the invention, as illustrated, without departing from the scope of the description of the accompanying claims. Furthermore, although the invention has been particularly described with regard to its exceptional features in relation to a facial sauna, it would be readily apparent to one skilled in the art that the features of the invention may be used in any industrial application wherein the vaporization of a liquid is required.

What is claimed is:

1. An apparatus for generating vapor from a liquid comprising:
    a housing having an inlet for receiving the liquid therethrough and an outlet for discharging vapor therefrom;
    a tank portion within said housing interconnected with said inlet for holding the liquid received through said inlet;
    an air vent tube in said housing interconnecting said tank portion with an external air supply;
    vapor generating means in said housing including heating means for heating a vaporization surface above the vaporization temperature of the liquid so as to generate at least some vapor from the liquid upon contact of the liquid with said vaporization surface, said vapor generating means communicating with said housing outlet for discharge of said vapor from said outlet;
    a conduit interconnecting said tank portion with said vapor generating means for delivery of the liquid thereto from said tank portion;
    an electric diaphragm pump for pumping the liquid from said tank portion through said conduit to said vaporization surface of said generating means, said pump including adjusting means for adjusting the pumping rate, said pump having an elastic diaphragm portion, said pump including an armature which operates said pump diaphragm, said pump being enclosed in said housing, said housing having an elastic wall portion immediately adjacent and confronting said pump such that said armature can be displaced to operate said pump diaphragm by manually inwardly deforming to a sufficient extent said elastic portion of said housing, to enable priming of said pump; and
    baffle means associated with said vapor generating means for preventing liquid from discharging with said generated vapor through said outlet.

2. The apparatus of claim 1 wherein said housing has a base portion which includes said inlet for filling said tank portion when said housing is in an inverted position.

3. The apparatus of claim 2 wherein said outlet is adapted for coupling to an attachment for dispersing the generated vapor.

4. The apparatus of claim 2 wherein said air vent tube communicates with said external air supply through said base portion.

5. The apparatus of claim 1 wherein said heating means includes an electric heater which heats said vaporization surface onto which said liquid is pumped.

6. The apparatus of claim 5 wherein said electric heater and vaporization surface are within a cartridge, said cartridge further including said baffle means.

7. The apparatus of claim 6 further comprising insulating means disposed between said housing and said cartridge.

8. The apparatus of claim 7 wherein said conduit includes a nozzle for spraying the liquid onto said heated vaporization surface.

9. The apparatus of claim 1 wherein said armature is connected to said pump diaphragm and said pump includes electromagnetic means for creating an alternating magnetic field, said armature being oscillated by said alternating magnetic field for producing pumping action with said pump diaphragm, an intake valve associated with said tank portion for receiving the liquid therefrom and an output valve operable by said diaphragm for transmitting the liquid therethrough to said vapor generating means, wherein both said input and output valves are one-way check valves.

10. The apparatus of claim 9 wherein said armature includes a magnet and said electromagnetic means includes a coil, and said adjusting means includes means for selectively pivoting said coil relative to said magnet for adjusting the pumping rate.

11. The apparatus of claim 9 wherein said intake valve is interconnected with said tank portion and said output valve is interconnected with said conduit.

12. The apparatus of claim 9 wherein said adjusting means for adjusting the pumping rate includes a control knob for regulating resistance in a variable resistor connected to said electromagnetic means for varying the current in said electromagnetic means.

13. The apparatus of claim 12 wherein said pumping rate is adjustable between about 2 to 5.5 cc/min.

14. The apparatus of claim 12 wherein said vapor generating means includes a cartridge having a cylindrical member with a boiler cavity therein defining said vaporization surface and an electric heater for heating said surface said baffle means including a pair of non-contacting 2-stage baffles located on opposite sides of said cartridge.

* * * * *